(12) United States Patent
Kim

(10) Patent No.: US 9,029,602 B2
(45) Date of Patent: May 12, 2015

(54) ANTI-MICROBIAL AND ANTI-STATIC SURFACE TREATMENT AGENT WITH QUATERNARY AMMONIUM SALT AS ACTIVE INGREDIENT AND METHOD FOR PREVENTING STATIC ELECTRICITY IN POLYMER FIBERS USING SAME

(75) Inventor: Seong Cheol Kim, Gyeongsan-si (KR)

(73) Assignee: Industry-Academic Cooperation Foundation, Yeungnam University, Gyeongsan-si, Gyeongsangbuk-do (KR)

( * ) Notice: Subject to any disclaimer, the term of this patent is extended or adjusted under 35 U.S.C. 154(b) by 76 days.

(21) Appl. No.: 13/824,130

(22) PCT Filed: Aug. 10, 2011

(86) PCT No.: PCT/KR2011/005865
§ 371 (c)(1),
(2), (4) Date: Mar. 15, 2013

(87) PCT Pub. No.: WO2012/036382
PCT Pub. Date: Mar. 22, 2012

(65) Prior Publication Data
US 2013/0183456 A1    Jul. 18, 2013

(30) Foreign Application Priority Data

Sep. 16, 2010  (KR) .......................... 10-2010-0091109
Apr. 19, 2011  (KR) .......................... 10-2011-0036313

(51) Int. Cl.
| | | |
|---|---|---|
| C07C 213/00 | (2006.01) | |
| C07C 215/00 | (2006.01) | |
| C07C 217/00 | (2006.01) | |
| C07C 211/63 | (2006.01) | |
| C08L 77/06 | (2006.01) | |

(52) U.S. Cl.
CPC .............. *C07C 211/63* (2013.01); *C08L 77/06* (2013.01)

(58) Field of Classification Search
CPC .... C07C 213/04; C07C 217/08; C07C 215/40
See application file for complete search history.

(56) References Cited

U.S. PATENT DOCUMENTS 4,822,529 A    4/1989    Saiki et al.

FOREIGN PATENT DOCUMENTS

| JP | 2005-154645 A | 6/2005 |
|---|---|---|
| KR | 10-2007-0113365 A | 11/2007 |
| KR | 10-0797098 B1 | 1/2008 |

OTHER PUBLICATIONS

Machine English Translation of Nomura et al. (Japanese Patent No. 2005154645, published Jun. 16, 2005).*
STN abstract of Nomura et al. (Japanese Patent No. 2005154645, published Jun. 16, 2005).*
English Translation of Nho (Noh) (Korean Patent No. 2007113365, published Nov. 29, 2007).*
STN abstract of Nho (Korean Patent No. 2007113365, published Nov. 29, 2007).*

* cited by examiner

*Primary Examiner* — Rosalynd Keys
*Assistant Examiner* — Jennifer C Sawyer
(74) *Attorney, Agent, or Firm* — Sherr & Jiang, PLLC

(57) ABSTRACT

Provided are an anti-static and anti-microbial surface treatment agent including a quaternary ammonium salt compound as an active ingredient and a method of preventing a polymer fiber from developing static electricity by using the surface treatment agent. The quaternary ammonium salt compound has excellent anti-static and anti-microbial effects for the prevention or improvement of static electricity in a polymer fiber. Accordingly, the quaternary ammonium salt compound is suitable for use as a fabric softener, or an anti-static agent, and also, provides anti-microbial effects to a polymer fiber.

1 Claim, No Drawings

ANTI-MICROBIAL AND ANTI-STATIC SURFACE TREATMENT AGENT WITH QUATERNARY AMMONIUM SALT AS ACTIVE INGREDIENT AND METHOD FOR PREVENTING STATIC ELECTRICITY IN POLYMER FIBERS USING SAME

CROSS REFERENCE TO PRIOR APPLICATIONS

This application is a National Stage Patent Application of PCT International Patent Application No. PCT/KR2011/005865 (filed on Aug. 10, 2011) under 35 U.S.C. §371, which claims priority to Korean Patent Application Nos. 10-2010-0091109 (filed on Sep. 16, 2010) and 10-2011-0036313 (filed on Apr. 19, 2011), which are all hereby incorporated by reference in their entirety.

TECHNICAL FIELD

The present invention relates to an anti-static and anti-microbial surface treatment agent including a quaternary ammonium salt compound as an active ingredient and a method of preventing a polymer fiber from developing static electricity by using the surface treatment agent.

BACKGROUND ART

Anti-static materials are used to remove static electricity or electrostatic charge, and an enhancement in charging with static electricity is associated with various problems in processing and using a variety of industrial products and materials. Charging with static electricity may cause attraction or repulsion of materials. In addition, an enhancement in charging with static electricity may cause attachment of waste or dust onto materials, thereby leading to manufacturing problems and pollution, and damaging performance of products.

An enhancement in charging of static electricity may be controlled by increasing electric conductivity of a material. This can be achieved by increasing ionic conductivity or electric conductivity. Typically, the accumulation of static electricity is controlled by adsorbing water molecules to increase electric conductivity. The adsorption is performed by, typically, adding water molecules to ambient air or using a water-absorbing anti-static agent, which is called a wetting agent. Most anti-static agents reduce electrostatic charges when charging with static electricity increases.

Known anti-static agents are, for example, organic amine and amide, aliphatic ester, an organic acid, a polyoxyethylene derivative, polyvalent alcohol, metal, carbon black, semiconductor, and various organic and inorganic salts. In addition, various surfactants may also be used, and they may be neutral or ionic.

Since various low molecular weight neutral anti-static agents have sufficiently high vapor pressure, such materials may be reduced in amounts by evaporation at high temperature, and thus, they are not suitable for use at high temperature. Various other neutral anti-static agents do not have sufficiently high thermal stability, so that they fail to perform their due functions under conditions for dissolving and processing a polymer and other high-temperature process conditions.

Various non-metallic anti-static agents are wetting agents that resort to adsorption and conductivity of water molecules to reduce charge. Accordingly, when humidity in the air is low, their effects are typically low. In addition, those anti-static agents are water-soluble, and accordingly, when materials are exposed to water molecules, the anti-static agents are easily removed. Accordingly, durability thereof is low.

Metal salts of inorganic, organic, and fluoro-organic anions are also suitable for use as an anti-static agent in a particular polymer composition. Due to costs and toxicity, and high affinity of an alkali metal cation, in particular, lithium with respect to water, alkali metal salts are the most commercially used. However, most metal salts do not have compatibility with polymers with middle or lower levels of polarity, such as polypropylene, polyester and polycarbonate. This incompatibility may decrease performance of an anti-static agent, may decrease physical properties of an anti-static agent to an unacceptable level, or may decrease transparency of finished polymer products to an unacceptable level. Ultimately, a metal salt for use as an anti-static agent is limited to a polymer matrix with high polarity or high hydrophilic property.

In response, the inventors of the present application searched for a quaternary ammonium salt compound that is suitable for use as an anti-static and anti-microbial agent and found that when a fiber is treated with a quaternary ammonium salt compound, static electricity of the fiber may be prevented or improved, thereby completing the present invention.

DETAILED DESCRIPTION OF THE INVENTION

Technical Problem

The present invention provides a novel anti-static and anti-microbial quaternary ammonium salt compound that prevents or improves static electricity of a fiber.

The present invention also provides a method of preventing a polymer fiber from developing static electricity, characterized by treating the polymer fiber with the quaternary ammonium salt compound.

Technical Solution

According to an aspect of the present invention, provided is an anti-static and anti-microbial surface treatment agent represented by Formula 1 below:

[Formula 1]

in Formula 1, $R_1$ is a functional group having one or more double bonds, and is selected from a C2 to C32 alkeny, a C1 to C32 alkylacryloyl, and a C1 to C32 alkylmetacryloyl, $R_2$ to $R_4$ are identical to or different from each other, include or do not include a double bond, and are each a C1 to C32 alkyl or hydroxyalkyl, a C6 to C32 aryl, a C7 to C32 benzyl, a C2 to C32 alkenyl, a C1 to C32 alkylacryloyl, a C1 to C32 alkylmetacryloyl, or a combination thereof, wherein those carbon chains may have an ester, amide, ether, sulfide, urethane, or urea bond as a covalent bond in their molecular structures, and X may be selected from F, Cl, Br, I, CN, $NO_3$, $CH_3COO$, $CF_3COO$, OH, ClO, $ClO_2$, $ClO_3$, SCN, $ClO_4$, $HCO_3$, $H_2PO_4$, $BF_4$, TFSI, $CF_3SO_3$, and $CH_3SO_3$.

Advantageous Effects

A quaternary ammonium salt compound according to the present invention has excellent anti-static and anti-microbial effects for the prevention or improvement of static electricity in a polymer fiber. Accordingly, when a polymer fiber is treated with the quaternary ammonium salt compound in the form of a fabric softener or an anti-static agent, static electricity of the polymer fiber may be prevented or improved, and also, the quaternary ammonium salt compound may be suitable for use in improving anti-microbial properties of a polymer fiber.

BEST MODE

The present invention provides an anti-static and anti-microbial surface treatment agent including a quaternary ammonium salt compound represented by Formula 1 below as an active ingredient:

[Formula 1]

in Formula 1, $R_1$ is a functional group having one or more double bonds, and is selected from a C2 to C32 alkeny, a C1 to C32 alkylacryloyl, and a C1 to C32 alkylmetacryloyl, $R_2$ to $R_4$ are identical to or different from each other, include or do not include a double bond, and are each a C1 to C32 alkyl or hydroxyalkyl, a C6 to C32 aryl, a C7 to C32 benzyl, a C2 to C32 alkenyl, a C1 to C32 alkylacryloyl, a C1 to C32 alkylmetacryloyl, or a combination thereof, wherein those carbon chains may have an ester, amide, ether, sulfide, urethane, or urea bond as a covalent bond in their molecular structures, and X may be selected from F, Cl, Br, I, CN, $NO_3$, $CH_3COO$, $CF_3COO$, OH, ClO, $ClO_2$, $ClO_3$, SCN, $ClO_4$, $HCO_3$, $H_2PO_4$, $BF_4$, TFSI, $CF_3SO_3$, and $CH_3SO_3$.

For example, $R_1$ may be allyl, $R_2$ to $R_4$ may be ethyl, and X may be Br or Cl.

In particular, the quaternary ammonium salt compound may provide, in addition to anti-static effects, anti-microbial effects.

The present invention also provides a method of preventing static electricity in a polymer fiber, including treating a polymer fiber with a surface treatment agent including the quaternary ammonium salt compound represented by Formula 1 as an active ingredient.

In detail, the method of preventing static electricity according to an embodiment of the present invention may include dipping a polymer fiber in a solvent; and treating the polymer fiber with a surface treatment mixture including a surface treatment agent including the quaternary ammonium salt compound represented by Formula 1 as an active ingredient, and a reaction catalyst.

In addition, the method of preventing static electricity according to an embodiment of the present invention may include treating a polymer fiber with a surface treatment mixture including a solvent, a surface treatment agent including the quaternary ammonium salt compound represented by Formula 1 as an active ingredient, and a reaction catalyst.

Examples of the reaction catalyst are cerium ammonium nitrate (CAN); $CeCl_3.7H_2O$/NaI; a tertiary amine-based basic catalyst, such as 1,8-diazabicyclo[5.4.0]undec-7-ene (DBU), 4-N,N-dimethylaminopyridine (DMAP), 3-hydroxyquinyclidine (3-HQD), 1,2,2,6,6-pentamethylpiperidine, or triethylamine (TEA); an acidic catalyst, such as $(CF_3SO_2)_2NH$, para-toluenesulfonic acid (PTSA), triflic acid, HCl, or $CH_3SO_3H$; an organometalic catalyst, such as Rh compound, Pd compound, Zn compound, Cu compound, Ni compound, Bi compound, or La compound; a pro-azaphosphatranes-based catalyst; a trialkylphosphines-based catalyst; $BF_3.Et_2O$; KF/alumina; $InBr_3$; and a biphenyldiamine-based catalyst.

Regarding the method of preventing static electricity, an amount of the quaternary ammonium salt compound may be in a range of about 0.1 to about 50 parts by weight based on 100 parts by weight of the polymer fiber. If the amount of the quaternary ammonium salt compound is outside the upper limit, thermal stability, mechanical properties, and thermo-keeping characteristics may decrease, and if the amount of the quaternary ammonium salt compound is outside the lower limit, the static electricity may not be effectively prevented.

In addition, an amount of the reaction catalyst may be in a range of about 0.01 to about 20 parts by weight based on 100 parts by weight of the polymer fiber. If the amount of the reaction catalyst is outside the upper limit, the reaction catalyst may remain after washing or a fiber may be discolored, and if the amount of the reaction catalyst is outside the lower limit, a quaternary ammonium salt may be insufficiently grafted or covalently bonded to a fiber.

The solvent may be any one of various solvents that wet or dissolve the polymer fiber and dissolve the reaction catalyst. Examples of the solvent are water, dimethylsulfoxide, ethanol, methanol, dimethylformamide, N-methylpyrrolidone, dichlorobenzene, tetrahydrofuran, dichloromethane, acetone, acetonitrile, toluene, and benzene, which may be used alone or in combination. The reaction catalyst may be treated at the temperature of about 5 to about 100° C., for example, at room temperature.

In addition, the method of preventing static electricity according to an embodiment of the present invention may further include, prior to or simultaneously with the treating of the polymer fiber with the surface treatment agent, forming a radical of the polymer fiber by using at least one treatment selected from (i) a treatment with a reaction catalyst, (ii) irradiation of gamma ray, (iii) irradiation of E-beam, (iv) irradiation of ion-beam, (v) irradiation of deep ultra violet (UV) light, and (vi) a plasma treatment.

In addition, the method of preventing static electricity according to an embodiment of the present invention may include forming a radical of the polymer fiber by using at least one treatment selected from (i) a treatment with a reaction catalyst, (ii) irradiation of gamma ray, (iii) irradiation of E-beam, (iv) irradiation of ion-beam, (v) irradiation of deep ultra violet (UV) light, and (vi) a plasma treatment; and adding the surface treatment agent including the quaternary ammonium salt compound represented by Formula 1 as an active ingredient to the radical of the polymer fiber to form a covalent bond with a double bond of the quaternary ammonium salt and one radical of the fiber or to form (graft) radical polymeration with a plurality of quaternary ammonium salt molecules and one radical of the fiber.

The fiber used in embodiments of the present invention may be natural fiber or synthetic fiber, and for example, a fiber having a hydroxy group, an amine group, or an imine group, but is not limited thereto.

MODE OF THE INVENTION

Hereinafter, embodiments of the present invention are described by referring to examples. However, the embodiments of the present invention are not limited to the examples.

Example 1

Synthesis of Quaternary Ammonium Salt Compound 1. 1. Synthesis of ABTEA ($R_1$=allyl, $R_2$, $R_3$ and $R_4$=ethyl, and X=Br)

0.1 mol of allylbromide and 0.105 mol of triethylamine were added to 100 mL of THF, and stirred at the temperature of 40° C. for one day. A synthesized ABTEA precipitated as a white solid, and the precipitated ABTEA was washed several times with THF to remove unreacted materials and a stabilizer.

$^1$H NMR (600 MHz, $D_2O$): δ5.96 (m, 1H), 5.74 (d, 1H), 5.70 (s, 1H), 3.84 (d, 1H), 3.30 (q, 6H), 1.31 (t, 9H)

2. 1. Synthesis of ACTEA ($R_1$=allyl, $R_2$, $R_3$ and $R_4$=ethyl, and X=Br)

0.1 mol of allyl chloride and 0.105 mol of triethylamine were added to 100 mL of THF, and then, a small amount of triphenyl phosphine or 1,2,2,6,6-pentamethylpyperidine was added thereto and the mixture was stirred at the temperature of 30° C. for 2 days. A synthesized ACTEA precipitated as a white solid, and the precipitated was washed several times with THF to remove unreacted materials and a stabilizer.

$^1$H NMR (600 MHz, $D_2O$): δ5.94 (m, 1H), 5.68 (d, 1H), 5.64 (s, 1H), 3.80 (d, 1H), 3.24 (q, 6H), 1.26 (t, 9H)

3. Synthesis of E2M (R=methacryloyl, $R_2$ and $R_3$=methyl, $R_4$=ethyl, X=Br)

0.1 mol of dimethylaminoethylmethacrylate and 0.11 mol of ethylbromide were added to 100 mL of THF and then reacted at the temperature of 30° C. for two days. The precipitated solid product was washed several times with THF to remove a polymerization inhibitor and unreacted materials, and then refrigerated in dark.

$^1$H NMR (300 MHz, $D_2O$): δ6.22 (d, 1H), 5.85 (d, 1H), 4.70 (t, 2H), 3.81 (t, 2H), 3.59 (m, 2H), 3.20 (s, 6H), 2.01 (s, 3H), 1.46 (t, 3H)

Example 2

Surface Treatment with Quaternary Ammonium Salt Compound 200 mL of water with a temperature of 30° C. was added to 8 g of a fabric (105-F01) manufactured according to ISO 105 of British James H. Heal Company, and then, waited until the fabric sufficiently wetted. The quaternary ammonium salts prepared according to Example 1 were each prepared at a weight ratio of 50% (4 g). Cerium ammonium nitrate was added thereto at a weight ratio of 2% (0.08 g) with respect to a quaternary ammonium. 4 g of each of the quaternary ammonium salts was dissolved in 20 mL of water and then added to the fiber to surface-treat the fiber.

Example 3

Surface Treatment with Quaternary Ammonium Salt Compound 8 g of nylon 66 (105-F03) manufactured according to ISO 105 of British James H. Heal Company was cut and then E-beam with an intensity of 50 to 500 kGy was irradiated thereto. The nylon was wet with a 0.5M solution of the quaternary ammonium salt (E2M, $R_1$=methacryloyl, $R_2$ and $R_3$=methyl, $R_4$=ethyl, and X=Br) prepared according to Example 1 and then was left to sit at a temperature of 60° C. to make a reaction occur in a vinyl pack while in contact with the air for 20 minutes to 4 hours. After the reaction proceeded, the synthesized fiber was washed with methanol by using a soxhlet apparatus for one day.

Example 4

Surface Treatment with Quaternary Ammonium Salt Compound 8 g of nylon 66 (105-F03), fabric (105-F01), and silk (105-F06) prepared according to ISO 105 of British James H. Heal Company was each cut and then E-beam with an intensity of 50 to 500 kGy was irradiated thereto in the atmospheric condition. The E-beam treated fabric samples were added to a three-neck-round flask and then evacuated to remove air therefrom. Nitrogen was added to 0.5 M solution of the quaternary ammonium salt (E2M, $R_1$=methacryloyl, R and $R_3$=methyl, $R_4$=ethyl, and X=Br) prepared according to Example 1 to remove oxygen therefrom and then placed in the vacuum flask and a reaction was performed while a temperature was maintained at 70° C. for one hour. After the reaction finished, the synthesized fiber was washed with methanol by using a soxhlet apparatus for one day.

Experimental Example 1

Identification of Static Electricity Prevention Effects

Korea Textile Development Institute was commissioned to analyze charging properties of the polymer fibers that were surface treated as in Example 2, and the charging properties were measured according to JIS L 1094 (a method of evaluating triboelectrification), and results thereof are shown in Table 1 below.

TABLE 1

| Treated fabric | | Abrasive cloth | Triboelectrification (V) Variant: weight ratio | | | | | Kind of ammonium salt |
| --- | --- | --- | --- | --- | --- | --- | --- | --- |
| | | | 50% | 25% | 10% | 5% | 2% | |
| Fabric | cotton | warp thread | 10 | 30 | 1030 | 2090 | 3420 | ABTEA |
| | | weft | 10 | 50 | 1180 | 3200 | 3380 | |
| | wool | warp thread | 10 | 10 | 160 | 1220 | 1620 | |
| | | weft | 0 | 20 | 390 | 1750 | 1860 | |
| | cotton | warp thread | 10 | | | | | ACTEA |
| | | weft | 10 | | | | | |
| | wool | warp thread | 10 | | | | | |
| | | weft | 10 | | | | | |

TABLE 1-continued

| | | | | | | |
|---|---|---|---|---|---|---|
| cotton | warp thread | 80 | | | | E2M |
| | weft | 70 | | | | |
| wool | warp thread | 10 | | | | |
| | weft | 10 or lower | | | | |

| | | Triboelectrification (V) Variant: time (min) | | | | |
|---|---|---|---|---|---|---|
| Abrasive cloth | | 1 minute | 5 minutes | 10 minutes | 30 minutes | 60 minutes |
| cotton | warp thread | 80 | 80 | 130 | 130 | 120 | E2M |
| | weft | 70 | 20 | 70 | 90 | 60 | 50% |
| wool | warp thread | 10 | 10 or lower | 60 | 150 | 130 | |
| | weft | 10 or lower | 10 or lower | 10 or lower | 70 | 110 | |

Triboelectrification of the nylon 66 with respect to time when the fiber was surface-treated with E-beam as in Examples 3 and 4 is shown in Table 2, and triboelectrification thereof with respect to fiber is shown in Table 3.

TABLE 2

| | | Triboelectrification (V) Variant: Time | | | | | |
|---|---|---|---|---|---|---|---|
| Abrasive cloth | | 20 min | 40 min | 1 hr | 2 hr | 4 hr | Remarks |
| cotton | warp thread | 6160 | 8750 | 3410 | 2780 | 1960 | Example 3 using E2M |
| | weft | 4510 | 8780 | 4910 | 6050 | 4640 | |
| wool | warp thread | 8400 | 7260 | 9930 | 7860 | 3860 | |
| | weft | 8680 | 5480 | 11620 | 4000 | 2690 | |

TABLE 3

| | | Triboelectrification (V) Variant: Fiber | | | |
|---|---|---|---|---|---|
| Abrasive cloth | | Silk | Nylon | Fabric | Remarks |
| Cotton | warp thread | 10 or lower | 10 or lower | 10 or lower | Example 4 using E2M |
| | weft | 10 or lower | 10 or lower | 10 or lower | |
| wool | warp thread | 10 or lower | 10 or lower | 10 or lower | |
| | weft | 10 or lower | 10 or lower | 10 or lower | |

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A method of preventing static electricity in a polymer fiber, comprising:

forming a radical of the polymer fiber by irradiation with E-beam; and adding a quaternary ammonium salt compound to the radical of the polymer fiber to form a covalent bond with a double bond of the quaternary ammonium salt and one radical of the fiber or to form radical polymerization with a plurality of quaternary ammonium salt molecules and one radical of the fiber, wherein the quaternary ammonium salt compound is represented by Formula 1 below as an active ingredient:

[Formula 1]

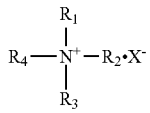

in Formula 1,
wherein the $R_1$ is allyl, the $R_2$ to $R_4$ are ethyl, and the X is Br.

* * * * *